(12) United States Patent
Paladini et al.

(10) Patent No.: US 7,087,781 B2
(45) Date of Patent: Aug. 8, 2006

(54) POLYAMINOMETHYLENEPHOS PHONATE DERIVATIVES

(75) Inventors: Massimo Paladini, Bergamo (IT); Francesco Spini, Bergamo (IT); Alessandro Scalvedi, Almé (IT); Daniele Tarallo, Segrate (IT); Jean Claude Valle, Bergamo (IT)

(73) Assignee: Giovanni Bozzetto S.p.A., Bergamo (IT)

( * ) Notice: Subject to any disclaimer, the term of this patent is extended or adjusted under 35 U.S.C. 154(b) by 0 days.

(21) Appl. No.: 10/522,858

(22) PCT Filed: Jul. 3, 2003

(86) PCT No.: PCT/IT03/00420

§ 371 (c)(1), (2), (4) Date: Apr. 4, 2005

(87) PCT Pub. No.: WO2004/011475

PCT Pub. Date: Feb. 5, 2004

(65) Prior Publication Data

US 2005/0171376 A1   Aug. 4, 2005

(30) Foreign Application Priority Data

Jul. 31, 2002  (IT)  ...................... MI2002A001706

(51) Int. Cl.
*C07F 9/28* (2006.01)

(52) U.S. Cl. .......................................... 562/14; 510/402

(58) Field of Classification Search ................... 562/14
See application file for complete search history.

(56) References Cited

U.S. PATENT DOCUMENTS

| | | |
|---|---|---|
| 3,925,245 A | 12/1975 | Harris et al. |
| 4,085,134 A | 4/1978 | Redmore |
| 4,187,245 A | 2/1980 | Redmore |
| 4,872,996 A | 10/1989 | Grierson et al. |
| 5,057,228 A | 10/1991 | Breen et al. |
| 5,261,491 A | 11/1993 | Stewart et al. |
| 5,490,942 A | 2/1996 | Kuczinski |
| 2003/0216275 A1 | 11/2003 | Crump et al. |

FOREIGN PATENT DOCUMENTS

| | | | |
|---|---|---|---|
| GB | 1392044 | * | 6/1971 |
| GB | 0479462 A1 | * | 4/1992 |
| SU | 643177 | | 1/1979 |

OTHER PUBLICATIONS

Wang, Rui et al., Chemical Abstracts, Jan. 31, 2000, vol. 2, No. 132, Abstract No. 54509, Columbus, OH.
Frigerio, M. et al., Prodotti sequestranti in tintura e stampa, Tinctoria, Mar. 1987, No. 3, pp. 57-64.

* cited by examiner

*Primary Examiner*—Paul A. Zucker
(74) *Attorney, Agent, or Firm*—Serafini Associates; Franco A. Serafini

(57) ABSTRACT

In one embodiment, a scale inhibitor comprising at least one polymethylenephosphonate derivative having the following formula:

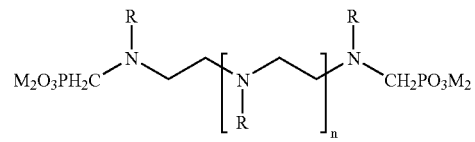

wherein n is a number, wherein M is hydrogen or a cation, wherein $R_1$, $R_2$, and $R_3$ are each independently selected from the group consisting of $CH_2PO_3M_2$, $CH_2R_4$, wherein $R_4$ is $CHOHCH_3$, $CHOHCH_2Cl$, or $CHOHCH_2OH$, $(CH_2)_m SO_3M$, wherein m is 3 or 4, and $CH_2CH_2R_5$, wherein $R_5$ is $CONH_2$, CHO, $COOR_6$, COOX, or CN, wherein $R_6$ is $CH_3$ or $C_2H_5$, and wherein X is an alkali metal or ammonium, and wherein at least one of $R_1$, $R_2$, and $R_3$ is not $CH_2PO_3M_2$. In another embodiment, a method for inhibiting scale formation in water, and in still another embodiment, a method for sequestering iron ions in a water systems, each of the methods comprising the step of providing the water with the above described polymethylenephosphonate derivative.

7 Claims, 2 Drawing Sheets

POLYAMINOMETHYLENEPHOS PHONATE DERIVATIVES

BACKGROUND OF THE INVENTION

1. Field of the Invention

The present invention relates to a new class of phosphonates and related salts, the method of preparation of the same and their utilization in the preparation of water additives to be used in different industrial fields. More specifically, the products and the processes according to the present invention provide new additives that prevent the segregation of solids from their aqueous solutions or dispersions by acting as precipitation inhibitors and dispersants.

2. Description of Related Art

Water in its natural state, as found in rivers, lakes and seas, and with the exeception of rain water, contains a certain quantity of metal ions and anions of different types and in various proportions, according to their origins. Such metal ions cause the formation of a precipitate, when water taken from its natural environment is used for industrial purposes. In industrial processes, water which is normally in equilibrium with the external environment is affected by different physical-chemical conditions, and if the concentration of salts under these new conditions exceeds the solubility product ("supersaturation"), salt precipitation is observed.

Such precipitating salts are generally formed by earth-alkali metals (Ca; Ba; Mg); among them Calcium—mostly as carbonate but also as sulfate—is mostly responsible for phenomena of incrustation in several industrial water applications.

The incrustation (not only limited to poory soluble salts) is generally called "SCALE" by water treatment experts.

Several factors cause supersaturation and thus the precipitation of aqueous solutions containing calcium carbonate. The $CaCO_3/CO_2/H_2O$ system is described schematically here in FIG. 1.

Calcium is present in all surface waters in the form of soluble bicarbonate ($HCO_3^-$) due to the absorption of carbon dioxide from the atmosphere. Any modification of such a system leads, in a more or less marked way, to precipitation of $CaCO_3$.

The causes for the precipitation of $CaCO_3$ can be classified as follows:

1. Concentration of the solution (evaporation of the aqueous phase);
2. Variations of temperature. By heating, the following transformation takes place:

3. Variations of the pH. An increase in the pH of the system results in the following transformation:

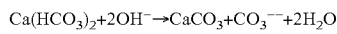

As far as cooling and/or heat-exchanger circuits are concerned, the incrustation (scale) formation mechanism can be attributed to a precipitation of salts from supersaturated solutions in the regions adjacent to the heat exchange surface of the system.

The effects of such uncontrolled precipitation are sometimes disastrous. For example, in cooling systems, where large volumes of water are used, the deposits of $CaCO_3$ accumulate in large quantity in the pipes, causing a reduction of the thermal exchange capacity and leading to a virtual occlusion of the pipes, making it necessary to remove the deposits by acidic treatment with consequent shutdown of the plant.

Moreover, the formation of a $CaCO_3$ incrustation facilitates the incorporation of solid particles that cannot be chemically removed (e.g. $SiO_2$) or the growth of bacteria and algae.

In order to overcome these disadvantages, pretreatments have been proposed in the prior art that provide for the preventive elimination of low-solubility salts by ionic exchange, precipitation, or by the use of suitable "sequestering agents" and suitable "scale inhibitors".

Preventive elimination is in most cases not economically acceptable because of the large volumes of water involved.

The same can be said for the chelating agents; it is well known that these substances form water-soluble complexes with the metal ions within a well defined stoichiometric molar ratio.

The preferred treatment in the prior art involves the use of suitable "scale inhibitors" that take advantage of the so called "Threshold Effect." The Threshold Effect was discovered by observing the behavior of inorganic polyphosphates that prevent the precipitation of the $CaCO_3$ from supersaturated solutions by means of sub-stoichiometric concentrations (Hatch and Rice, *Indust. Eng. Chem.*, 31, 51–53 (1939); Reitemeier and Buehrer, *J. Phys. Chem.*, 44 (5), 535–536 (1940); Fink and Richardson U.S. Pat. No. 2,358,222; and Hatch, U.S. Pat. No. 2,539,305).

The mechanism by which precipitation is inhibited is not completely understood today, although the absorption of an inhibitor onto the crystalline surface seems necessarily to be the first step in the inhibition process. The molecules of the inhibitor are attracted on the growing crystalline surface by the presence of metal cations such as Ca, Mg, Ba, for which they have a great affinity.

Once the molecules of the inhibitor are adsorbed, such molecules reside on the surface of the crystal, thus disturbing the regularity of its growth.

If all of this happens during the "nucleation" phase, i.e. during the stage in which a certain number of molecules in solution begins to aggregate in order to give rise to a crystal nucleus, the inhibitor can disturb nuclear growth to such an extent as to make the nucleus redissolve.

Such ability, exercised by various polyelectrolytes, is particularly marked in the case of phosphonates, which moreover combine corrosion inhibition functions with great resistance to hydrolysis.

However, for every operating condition, there is a limit to the molar ratio between inhibitor and metal. In fact, by increasing the phosphonate quantity beyond a certain limit, precipitation of insoluble calcium salts of phosphonates is observed; in such "turbidity" zone, the phosphonate is no longer active. The effectiveness of the phosphonates at various inhibitor/metal ratios is shown schematically in FIG. 2, wherein the x-axis relates to the molar ratio between metal and inhibitor, while the y-axis relates to the turbidity measured nephelometrically.

Furthermore, it is well known that it is necessary to provide for more effective recovery cycles of industrial water—above all because of an increasing use of water resources—in order to reduce both the quantity of water used and the environmental impact of the treatment agents.

BRIEF SUMMARY OF THE INVENTION

The present invention relates to a new class of phosphonates, to a simple and economic process for the production of said new class of phosphonates, and to the use of said phosphonates in water treatment applications. Therefore, the main object of the present invention is a new class of phosphonates that can be used for water treatment.

The compounds that form the object of the present invention are the derivatives of polyaminomethylenephosphonates having the following general formula:

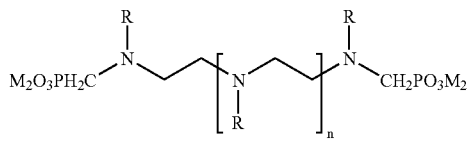

where n is preferably a number between 2 and 15000, most preferably between 2 and 50; wherein M is hydrogen or a cation, wherein $R_1$, $R_2$, and $R_3$ are each independently selected from the group consisting of $CH_2PO_3M_2$, $CH_2R_4$, wherein $R_4$ is $CHOHCH_3$, $CHOHCH_2Cl$, or $CHOHCH_2OH$, $(CH_2)_mSO_3M$, wherein m is 3 or 4, and $CH_2CH_2R_5$, wherein $R_5$ is $CONH_2$, CHO, $COOR_6$, COOX, or CN, wherein $R_6$ is $CH_3$ or $C_2H_5$, and wherein X is an alkali metal or ammonium, and wherein at least one of $R_1$, $R_2$, and $R_3$ is not $CH_2PO_3M_2$.

More particularly, the compounds that form the object of the present invention are derivatives of polyaminomethylenephosphonates according to the above mentioned formula, wherein the polyamine chain may be linear or branched, wherein n is an integer or fractional integer which is, or on average is, from about 2 to about 15000, wherein $M_2$ may be hydrogen or a suitable cation such as alkali metal or ammonium, and wherein each R group my be the same or different and is independently selected from the following classes:

1. $CH_2PO_3M_2$, wherein M may be hydrogen or a suitable cation such as alkali metal or ammonium;
2. $CH_2R$, wherein R=$CH_2OH$; $CHOHCH_3$; $CHOHCH_2Cl$; $CHOHCH_2OH$;
3. $(CH_2)_nSO_3M$, wherein n=3–4, and where M may be hydrogen or a suitable cation such as alkali metal or ammonium;
4. $CH_2CH_2R$, wherein R=$CONH_2$, CHO, $COOR_1$, COOX, CN, where $R_1$=$CH_3 \div C_2H_5$, and wherein X may be hydrogen or a suitable cation such as alkali metal or ammonium, with the condition that at least one of substituent R should be different from the methylenephosphonated group (i.e.: other than —$CH_2PO_3M_2$).

A particular advantage of the class of phosphonates that are the object of this invention is that such compounds do not show "Turbidity Zone" and are, therefore, to be considered non calcium-sensitive at any concentration and temperature tested.

These compounds are also effectives at high pH values (>10).

This is a very important aspect of the invention, since calcium tolerance of the traditional scale inhibitors like HEDP or ATMP quickly reduces with an increasing of the pH; in particular, this is important today because water treatment processes are carried out at higher pH values than in the past. In fact, a higher pH reduces the effects of corrosion, which is more marked at lower pH values.

The advantages of the new class of phosphonates that are the object of the present invention can be summarised as follows:

1. A threshold effect that is typical of the phosphonates, i.e. inhibition of precipitation from solutions supersaturated with $CaCO_3$ and/or $CaSO_4$ at sub-stoichiometric concentrations of the inhibitor;
2. Non calcium-sensitivity, because increases in pH and concentration of calcium strongly affect the tolerance of the standard phosphonates (HEDP, ATMP, etc.) to calcium, increasing the possibility of precipitation of poorly soluble calcium-phosphonate salts.
3. A dispersing effect better than traditional phosphonates. This new class of phosphonates behaves like acrylic polymers, accting as dispersants and deflocculants, and stabilizing colloidal systems which remain steadily dispersed for long periods.
4. A corrosion inhibition that is comparable to that of the standard phosphonates.
5. A chelating effect that is comparable to that of the standard phosphonates.
6. A hydrolytic stability that is similar to conventional phosphonates.

As shown in point 3) above, in addition to the threshold effect, the products object of the present invention shows a high "dispersing ability". This property becomes evident when the sequestering power is determined by the traditional "HAMPSHIRE" method, and by using this method it is not possible to identify an end-point during the titration with calcium acetate.

This property also suggests a potential application for this new class of phosphonates as deflocculants, to be used in a certain number of processes and applications where this new class of phosphonates can act as a stabilizer for different knds of dispersions like pigments ($TiO_2$), kaolin and drilling mud, and in the industrial and domestic detergent field for their ability to disperse dirt particles. From a general point of view, because of their particular properties, the products according to the present invention can be used for:

a reverse osmosis system;
scale removal;
scale prevention and corrosion control;
boiler cleaning;
bottle washing;
hard surface cleaners;
cooling system;
slurry dispersion;
textile processing;
sanitary cleaners;
paints;
secodnary oil recovery;
oil drilling muds;
laundry detergents;
industrial cleaners;
peroxide stabilisation;
metal finishing;
metal cleaners;
geothermal water;
setting retardants for concrete;
pulp & paper bleaching;
car washing;
flash desalination.

An object of the present invention is also a simple and economic process for the preparation of the phosphonates and their utilization in the above mentioned fields, particularly as inhibitors of the formation, deposition, and adhesion of incrustations caused by insoluble salts of alkali-earth metals, in particular $Ca^{++}$ and $Mg^{++}$, on metal surfaces of aqueous equipment systems (cooling towers, boilers, gas scrubbers, etc.)

DETAILED DESCRIPTION OF THE INVENTION

Figure 1:
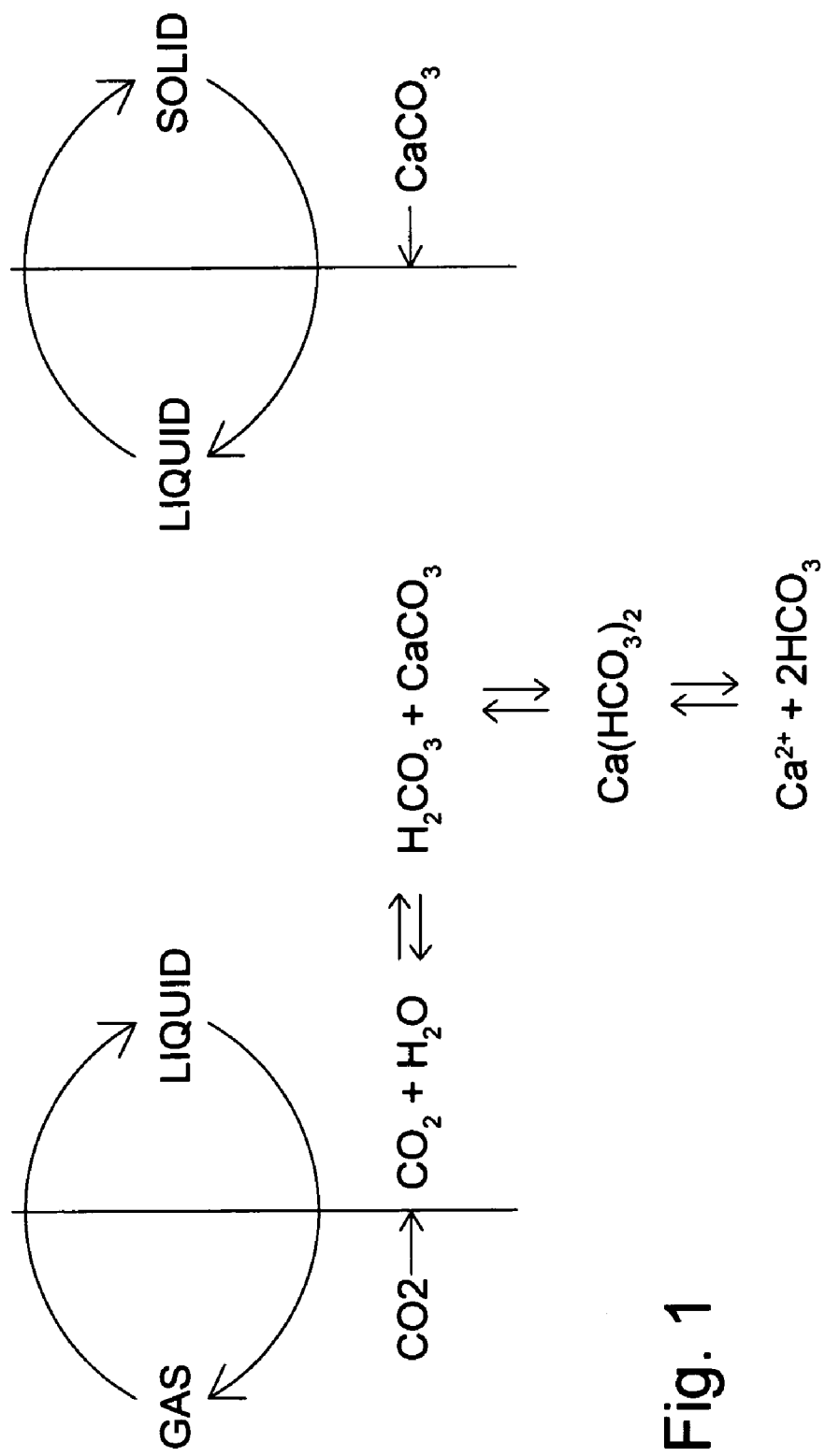
FIG. 1 is a schematic illustration of a supersaturation cycle.
Figure 2:
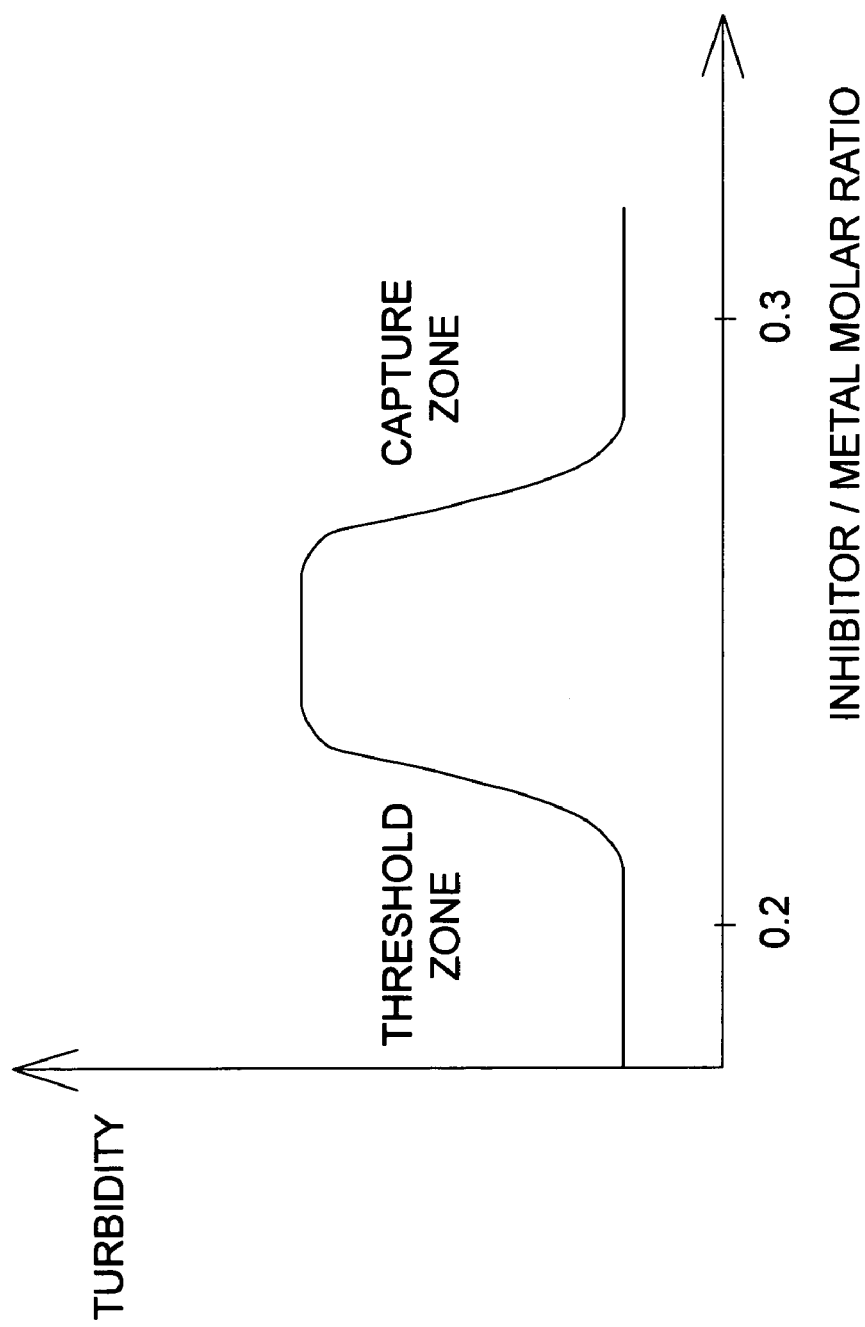
FIG. 2 is a chart illustration of the effectiveness of phosphonates as nuclear growth inhibitors at various inhibitor/metal ratios.

Detailed descriptions of embodiments of the invention are provided herein. It is to be understood, however, that the present invention may be embodied in various forms. Therefore, the specific details disclosed herein are not to be interpreted as limiting, but rather as a representative basis for teaching one skilled in the art how to employ the present invention jn virtually any detail system, structure, or manner.

More specifically, embodiments of the present invention will now be described with particular reference to the preparation and to the use of products and processes for the preparation and the stabilization of aqueous dispersions, even though the scope of the invention should not be limited to such possible applications.

In one embodiment of the invention, polyaminomethylenephosphonate derivatives are prepared by a phosphonomethylation reaction of polyamine or mixtures of polyamines by means of the Mannich reaction illustrated hereunder:

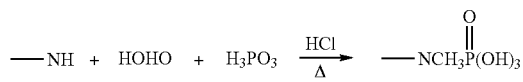

The phosphonomethylation reaction of amines according to Mannich is described in the literature, eg: K. Moedritzer and R. Irani, *J. Organic. Chem.* 31 (5) 1603–7.

A typical procedure provides for the amine to be slowly added to a mixture of a phosphorus-based acid and hydrochloric acid. The reaction mixture thus obtained is heated to reflux with the addition of formaldehyde. The reaction time can vary from 1 to 5 h.

The derivatives of the polyaminomethylenephosphonate in this embodiment are added to the aqueous systems in quantities between 2 and 50 mg/l, in order to inhibit precipitation, deposition and adhesion of scale, especially of $CaCO_3$.

Inhibiting the precipitation and formation of deposits includes the threshold effect, dispersion, solubilization or modification of the precipitate's morphology. Inhibiting adhesion defines just that scale is easily removed, e.g. by simple washing/rinsing and not by mechanical or chemical treatment, because the incrustation is not strongly bonded to the underlying surface.

The term "scale" includes incrustation formed by $CaCO_3$, $CaSO_4$, $BaSO_4$ deposits and can be extended in a generalized manner to include all low-solubility salts of several cations (Mg, Fe, etc.).

The term "aqueous systems" refers to industrial and/or commercial systems that use water in heat-exchange processes and includes cooling towers, boilers, desalination systems, gas scrubbers; furthermore, processes of desalination by reverse osmosis (RO) are included.

Of particular importance are systems operating in severe conditions, such as high pH and high concentrations of calcite ($CaCO_3$). The preparation and the application of the polyaminomethylenephosphonate derivatives according to the present embodiment are illustrated in the following examples, which will clarify their applications, but without limiting the scope of the invention.

Example 1

Into a suitable reaction vessel 350-g of triethylenetetramine were charged; thereafter the reaction mixutre was heated at 90–95° C.

Ethylene oxide was than added stepwise at such a rate that, with external cooling applied, the temperature did not exceed 100° C.

211 g of ethylene oxide were added over a period 1½ hours. The resultant product was then converted in the phosphonomethylated derivates according to Mannich's reaction.

With the same synthetic path is possible to obtain β hydroxyethyl derivates of linear or branched polyamines or a mixture thereof with an appropriate ratio. Other compounds according to the present embodiment can be prepared according to the above described procedure by using propylene oxide instead of ethylene oxide (β hydroxy propyl derivates).

Example 2

Into a suitable reaction vessel 292 g of triethylenetetramine were charged.

Under stirring conditions, acrylonitrile was than added stepwise at such a rate that, with external cooling applied, the temperature did not exceed 50° C.

212 g of acrylonitrile were added over a period 2 hours. The resultant product was than converted into phosphonomethylated derivates according to Mannich's reaction.

With the same synthetic path is possible to obtain β cyanoethyl derivates of linear or branched polyamines or mixture thereof with an appropriate ratio.

Example 3

Into a suitable reaction vessel 292 g of triethylenetetramine were charged.

Under stirring, 488 g of 1,3-propane sultone, dissolved in 1140 g of methanol, was added dropwise at a tempearture between 40–50° C. After 2 hours, the methanol was removed by evaporation to dryness and the residue dissolved in water. The resultant product was than converted into phosphonomethylated derivates according to Mannich's reaction.

With the same synthetic path is possible to obtain N-(sulfo propane)amino derivatives of linear or branched polyamines or a mixture thereof with an appropriate ratio.

Other compounds according to the present embodiment can be prepared according to the above described procedure by using epichlorohydrin or other different oxiranes derivatives instead of 1,3 propane sultone.

Example 4

Into a suitable reaction vessel 234 g of compound of example 1 were added to a 70% a phosphorus-based acid solution (478 g) as well as 32% of hydrochloric acid (342 g). The mixture thus obtained was heated to reflux, 340 g of 37% aqueous formaldehyde solution were added dropwise in the course of about 1 hr, and the reaction mixture was kept at the reflux temperature for 1 additional hr. 300 g of volatile substances were then removed from the reaction mixture by distillation. The final product obtained was a viscous fluid having an active substance of 50%. Infrated analysis of the product showed the presence of methylenephosphonic amine groups, while $P^{31}$ NMR analysis indicated that at least 90% of the amine groups had been phosphonomethylated. The impurities included unreacted phosphorus-based acid, phosphoric acid and other unidentified compounds.

By following the same synthetic method, phosphonometilated derivatives of polyamine may be obtained or a mix of polyamine having an R group selected from the following class:

1. $CH_2PO_3M_2$, wherein M may be hydrogen or an suitable cation such as alkali metal or ammonium;
2. $CH_2R$, wherein $R=CH_2OH$; $CHOHCH_3$; $CHOHCH_2Cl$; $CHOHCH_2OH$
3. $(CH_2)_nSO_3M$, wherein $n=3 \div 4$ where M may be hydrogen or a suitable cation such as alkali metal or ammonium;
4. $CH_2CH_2R$, wherein $R=CONH_2$, CHO, $COOR_1$, COOX, CN, wherein $R_1=CH_3 \div C_2H_5$, and wherein X may be hydrogen or a suitable cation such as alkali metal or ammonium, wherein preferably at least one or more than one substituent R is different from the methylenephosphonated group.

Example 5

This example is related to the threshold effect on $CaCO_3$ at pH=10, T=70° C., 100 ppm of $CaCO_3$ This method describes the procedure for the determination of the threshold effect, that is, the ability of a dispersing agent, present in substoichiometric amounts, to inhibit the precipitation of solutions supersaturated with calcium carbonate in deionized water.

This method measures the efficiency of a dispersant by titration of the calcium ion remaining in a solution supersaturated with $CaCO_3$ respectively before and after treatment in an oven at 70° C. The greater the calcium concentration after the period in the oven, the greater the efficiency of the dispersant in preventing precipitation of the $CaCO_3$.

Increasing substoichiometric amounts of phosphonate are dissolved in solutions containing $[Ca^{++}]$ and $[CO_3^{--}]$ obtained by mixing suitable $CaCl_2$ and $Na_2CO_3$ solutions.

The precipitation of calcium carbonate is measured by titration of the filtered solution. The results obtained are summarised in Table 1.

TABLE 1

Operating Conditions:
100 ppm $CaCO_3$; pH = 10; T = 70° C.; 24 h
Inhibition %

| Inhibitor | 0.25 ppm | 0.5 ppm | 1 ppm |
|---|---|---|---|
| Example 4 | 72 | 97 | 99 |
| HEDP | 74 | 99 | 100 |
| ATMP | 75 | 99 | 100 |
| DTPMP | 65 | 85 | 100 |
| PBTC | 90 | 100 | 100 | wherein:
HEDP = Hydroxy-ethylydene-1,1-diphosphonic Acid;
ATMP = Amino-tris Methylenephosphonic Acid;
DTPMP = Diethylenetriamine penta (methylenephosphonic acid);
PBTC = Phosphono Butane tris Carboxylic Acid.

Example 6

This example relates to the $CaCO_3$ threshold effect at pH=11.5, T=40° C., 400 ppm of $CaCO_3$ Following the method described in example 5, the following results were obtained:

TABLE 2

Operating Conditions:
400 ppm $CaCO_3$; pH = 11.5; T = 40° C.; 24 h
Inhibition %

| Inhibitor | 40 ppm | 80 ppm | 200 ppm | 400 ppm | 450 ppm |
|---|---|---|---|---|---|
| Example 4 | 0 | 35 | 90 | 92 | 95 |
| ATMP | 0 | 35 | 40 | 60 | 65 |
| DTPMP | 0 | 35 | 83 | 80 | 80 |
| PBTC | 0 | 30 | 42 | 92 | 95 |

Example 7

This example relates to $CaSO_4$ threshold effect at pH=7; T=70° C.; 6800 ppm of $CaSO_4$.

Following the method described in example 5, the solution of $CaSO_4$ was prepared starting from $CaCl_2$ and $Na_2SO_4$. The results obtained are summarized hereunder:

TABLE 3

Operating Conditions:
6800 ppm $CaSO_4$; pH = 7; T = 70° C.; 24 h
Inhibition %

| Inhibitor | 0.5 ppm | 1 ppm | 2 ppm | 5 ppm | 10 ppm |
|---|---|---|---|---|---|
| Example 4 | 10 | 10 | 90 | 100 | 100 |
| DTPMP | 10 | 22 | 75 | 95 | 100 |

Example 8

This example relates to $CaSO_4$ threshold effect at pH=7; T=70° C.; 6800 ppm of $CaSO_4$+6000 ppm of $Ca^{++}$.

Following the method described in example 4, a solution of $CaSO_4$ was prepared starting from $CaCl_2$ and $Na_2SO_4$. The results obtained are summarized in Table 4.

TABLE 4

Operating Conditions:
6800 ppm $CaSO_4$ + 6000 ppm di $Ca^{++}$; pH = 7; T = 70° C.; 24 h
Inhibition %

| Inhibitor | 2 ppm | 5 ppm | 10 ppm |
|---|---|---|---|
| Example 4 | 15 | 91 | 99 |
| DTPMP | 22 | 45 | 96 |

Example 9

This example relates to $CaSO_4$ threshold effect at pH=7; T=90° C.; 6800 ppm of $CaSO_4$.

Following the method described in example 5, a solution of $CaSO_4$ was prepared starting from $CaCl_2$ and $Na_2SO_4$. The results obtained are summarized in Table 5.

TABLE 5

| | Operating Conditions: 6800 ppm $CaSO_4$; pH = 7; T = 90° C.; 24 h Inhibition % | | | | |
|---|---|---|---|---|---|
| Inhibitor | 0.5 ppm | 1 ppm | 2 ppm | 5 ppm | 10 ppm |
| Example 4 | 0 | 5 | 18 | 85 | 99 |
| DTPMP | 0 | 0 | 5 | 73 | 90 |

Example 10

This example relates to $CaSO_4$ threshold effect at pH=7; T=90° C.; 6800 ppm of $CaSO_4$+6000 ppm of $Ca^{++}$.

Following the method described in example 5, a solution of $CaSO_4$ was prepared starting from $CaCl_2$ and $Na_2SO_4$. The results obtained are summarized in Table 6.

TABLE 6

| | Operating Conditions: 6800 ppm $CaSO_4$ + 6000 ppm di $Ca^{++}$; pH = 7; T = 90° C.; 24 h Inhibition % | | | | |
|---|---|---|---|---|---|
| Inhibitor | 0.5 ppm | 1 ppm | 2 ppm | 5 ppm | 10 ppm |
| Example 4 | 10 | 15 | 18 | 91 | 99 |
| DTPMP | 0 | 0 | 8 | 38 | 45 |

Example 11

This example relates to calcium-sensitivity. The Grace "CLOUD POINT TEST" was used for testing the calcium-sensitivity. This simple method allows calcium-sensitivity to be verified visually by estimating the turbidity point of an inhibitor solution in a concentrated calcium solution. The inhibitor is added at increasing amounts to hard water having the following characteristics: 500 ppm of $Ca^{++}$ (as $CaCl_2$), pH=8.3 (0.05 M of boric buffer), at a temperature of 60° C. and 100° C. for 24 h.

The turbidity of solutions after 24 hours was observed. The observation confirmed that the turbidity is greater at increasing amounts of inhibitor. The results obtained are summarized in Tables 7 and 8.

TABLE 7

| | 500 ppm $CaCO_3$; pH = 8.3; T = 60° C. Inhibitor Dose | | | |
|---|---|---|---|---|
| Inhibitor | 10 ppm | 30 ppm | 50 ppm | 100 ppm |
| Example 4 | clear | clear | clear | clear |
| ATMP | clear | turbid | precipitate | precipitate |

TABLE 8

| | 500 ppm $CaCO_3$; pH = 8.3; T = 100° C. Inhibitor Dose | | | |
|---|---|---|---|---|
| Inhibitor | 10 ppm | 30 ppm | 50 ppm | 100 ppm |
| Example 4 | clear | clear | clear | clear |
| AMTP | precipitate | precipitate | precipitate | precipitate |

Example 12

This example relates to $Fe^{3+}$ sequestering. The measurement of the sequestering power of iron is difficult both for traditional phosphonates and for the polyaminomethylene-phosphonate derivatives according to the present embodiment, because both products have considerable dispersing ability, and if we considerer the colloidal aspect of the ferric hydrate, it is clear how difficult it could be to distinguish between the dispersed iron and the iron effectively sequestered. It is well known that a very fine dispersion is very similar to a solution. It must be said that often, in practical applications, an effective dispersion is as useful as a true sequestration.

The method involves the addition of a known quantity of solution of ferric ions to an aqueous solution of inhibitor at constant pH. After 24 hours under agitation, the aspect of the sample is evaluated. The samples where a precipitate is present after 24 hours of agitation were considered "precipitated," and so the first clear sample was considered in order to attribute a sequestring value. The results obtained are summarised in Table 9.

TABLE 9

| | $Fe^{3+}$ sequestering power expressed as mg $Fe^{3+}$/g of product | | | | | | | |
|---|---|---|---|---|---|---|---|---|
| Inhibitor | pH = 5 | pH = 6 | pH = 7 | pH = 8 | pH = 9 | pH = 10 | pH = 11 | pH = 12 |
| Example 4 | 0 | 60 | 180 | 200 | 260 | 360 | 200 | 20 |
| HEDP | 240 | 280 | 320 | 360 | 800 | 800 | 1200 | 1200 |
| ATMP | 40 | 60 | 100 | 120 | 140 | 180 | 120 | 0 |
| DTPMP | 40 | 60 | 80 | 140 | 220 | 130 | 60 | 20 |

The above data should be carefully evaluated, because the method utilized does not allow a dispersion to be distinguished from a true chelation. However, an internal comparison indicated that traditional phosphonates and the derivatives object of the present invention were equally effective in the control of ferric ion.

The present invention further addresses the problem of corrosion inhibition.

The corrosion of metal equipment is an almost universal problem for aqueous systems. Two distinct areas coexist on a metal surface, an anode and a cathode, which may be situated very close to each other and set up an electrical circuit with consequent Redox reactions leading to the solubilization of the metals. MOre particularly, iron surfaces are transformed into water-soluble $Fe^{2+/3+}$ ions. The corrosion, and therefore the loss of metal from part of the structure, takes place only in the anodic zone.

Without entering into the detail of the corrosion phenomenon, it is clear, however, that the damage caused by corrosive phenomena can be considerable in extent. Various methodologies and various products have been developed over time to address the problems related to the entity and various origins of corrosive phenomena. One of the more widespread methodologies involves the use, in aqueous phase, of suitable "corrosion inhibitors". These compounds may be organic or inorganic films or protective barriers between the metal surface and the of corrosion medium. Such a protective film can be developed by the following means:

a. Precipitation of an inhibitor onto the metal surface;
b. Passivation of the metal surface;
c. Adsorption of an inhibitor onto the metal surface through the electronic lone pair a donor element (N, S, O, P).

Example 13

In the following example, a simple test is described for evaluating the efficiency of the compounds according to the present embodiment as corrosion inhibitors. The operating conditions and the procedure used in the test are indicated below:

Taking water with 30 French degrees of hardness, bringing it at pH=8.5 with diluted NaOH and than adding the desired quantity of inhibitor;

Adding carefully cleaned and weighed steel coupons to the solution.

The test lasts 5 days with a constant airflow bubbled through the solution.

After 5 days, weighing the test pieces and estimating the loss in weight.

The results obtained are summarised in the following table:

TABLE 10

| Inhibitor | % weight loss after 5 days |
|---|---|
| Example 4 | 0.25 |
| ATMP | 0.45 |
| HEDP | 0.3 |
| Blank | 0.7 |

The invention claimed is:

1. A scale inhibitor comprising at least one polymethylenephosphate derivative having the following formula:

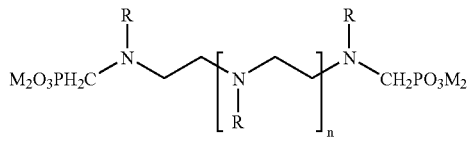

wherein n is an integer comprised between 2 and 15000,
wherein M is a hydrogen or a cation,
wherein $R_1$, $R_2$, and $R_3$ are each independently selected from the group consisting of,
$CH_2PO_3M_2$,
$CH_2R_4$, wherein $R_4$ is $CHOHCH_3$, $CHOHCH_2Cl$, or $CHOHCH_2OH$,
$(CH_2)_mSO_3M$, wherein m is 3 or 4, and
$CH_2CH_2R_5$, wherein $R_5$ is $CONH_2$, CHO, $COOR_6$, COOX, or CN, wherein $R_6$ is $CH_3$ or $C_2H_5$, and wherein X is an alkali metal or ammonium, and
wherein at least one of $R_1$, $R_2$, and $R_3$ is not $CH_2PO_3M_2$.

2. The scale inhibitor according to claim 1, wherein at least one of the $CH_2PO_3M_2$ moieties in a terminal position on the molecule is replaced by a moiety selected from the group consisting of $CH_2R_4$, $(CH_2)_mSO_3M$, and $CH_2CH_2R_5$.

3. The scale inhibitor of claim 1, wherein the polyaminomethylenephosphonate derivative is produced by a process of phosphonomethylation of polyamine derivatives employing the Mannich reaction.

4. The precipitation inhibitor according to claim 1, wherein M is an alkali metal or ammonium.

5. A method for inhibiting scale formation in water, the method comprising the step of adding to the water a scale inhibitor comprising at least one polymethylenephosphonate derivative having the following formula:

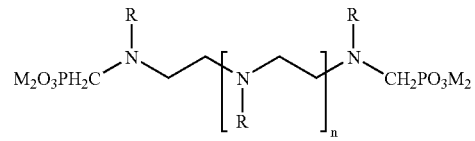

wherein n is an integer comprised between 2 and 15000,
wherein M is hydrogen or a cation,
wherein $R_1$, $R_2$, and $R_3$ are each independently selected from the group consisting of,
$CH_2PO_3M_2$,
$CH_2R_4$, wherein $R_4$ is $CHOHCH_3$, $CHOHCH_2Cl$, or $CHOHCH_2OH$,
$(CH_2)_mSO_3M$, wherein m is 3 or 4, and
$CH_2CH_2R_5$, wherein $R_5$ is $CONH_2$, CHO, $COOR_6$, COOX, or CN, wherein $R_6$ is $CH_3$ or $C_2H_5$, and wherein X is a an alkali metal or ammonium, and
wherein at least one of $R_1$, $R_2$, and $R_3$ is not $CH_2PO_3M_2$.

6. The method according to claim 5, further comprising the step of precipitating the polymethylenephosphonate derivative on a metal surface in contact with the water, thereby preventing corrosion of the metal surface.

7. A method for sequestering iron ions in a water system, the method comprising the step of providing the water in the water system with a scale inhibitor comprising at least one polymethylenephosphonate derivative having the following formula:

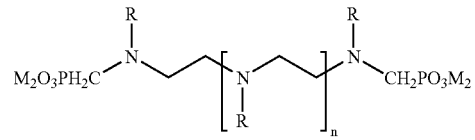

wherein n is an integer comprised between 2 and 15000,
wherein M is hydrogen or a cation,
wherein $R_1$, $R_2$, and $R_3$ are each independently selected from the group consisting of,
$CH_2PO_3M_2$,
$CH_2R_4$, wherein $R_4$ is $CHOHCH_3$, $CHOHCH_2Cl$, or $CHOHCH_2OH$,
$(CH_2)_mSO_3M$, wherein m is 3 or 4, and
$CH_2CH_2R_5$, wherein $R_5$ is $CONH_2$, CHO, $COOR_6$, COOX, or CN, wherein $R_6$ is $CH_3$ or $C_2H_5$, and wherein X is an alkali metal or ammonium, and
wherein at least one of $R_1$, $R_2$, and $R_3$ is not $CH_2PO_3M_2$.

* * * * *